United States Patent [19]

Lenke et al.

[11] Patent Number: 4,777,183

[45] Date of Patent: Oct. 11, 1988

[54] USE OF ANIPAMIL

[75] Inventors: Dieter Lenke, Ludwigshafen; Claus D. Mueller, Viernheim, both of Fed. Rep. of Germany

[73] Assignee: Knoll AG, Ludwigshafen, Fed. Rep. of Germany

[21] Appl. No.: 104,216

[22] Filed: Oct. 5, 1987

[30] Foreign Application Priority Data

Oct. 9, 1986 [DE] Fed. Rep. of Germany ....... 3634389

[51] Int. Cl.$^4$ .......................................... A61K 31/275
[52] U.S. Cl. ................................. 514/523; 514/824
[58] Field of Search ............................. 514/523, 824

[56] References Cited

U.S. PATENT DOCUMENTS

| | | | |
|---|---|---|---|
| 3,261,859 | 7/1966 | Dengel | 558/390 |
| 4,438,131 | 3/1984 | Ehrmann et al. | 514/523 |
| 4,593,042 | 6/1986 | Liang | 514/523 |
| 4,596,820 | 6/1986 | Raschack et al. | 514/523 |

OTHER PUBLICATIONS

"Verapamil Suppresses Atherosclerosis in Cholesterol-Fed Rabbits", by Jean-Lucien Rouleau, et al., *J. Am. Coll. Cardiol.* 1(6), 1453–1460 (1983).

"Mechanism of Protection from Atherosclerosis by Verapamil in the Cholesterol Fed Rabbit", by Steven L. Blumlein, et al., *The Am. J. of Cardiology* 54, pp.884–889 (1984).

*Primary Examiner*—Allen J. Robinson
*Attorney, Agent, or Firm*—Oblon, Fisher, Spivak, McClelland & Maier

[57] ABSTRACT

Anipamil and its salts with physiologically tolerated acids are used for the preparation of drugs having antiarteriosclerotic properties and in the treatment of arteriosclerosis.

1 Claim, No Drawings

USE OF ANIPAMIL

The present invention relates to a novel use of anipamil (1,7-bis-(3-methoxyphenyl)-3-methylaza-7-cyanononadecane).

Anipamil is disclosed in European Laid-Open Application No. 64,158, which states that the compound is suitable for the treatment of functional disorders of the cardiovascular system, cardiomyopathies and angiopathies. Other indications stated for anipamil are hypoxic and isohemic heart disease, myocardial damage not of coronary origin, high blood pressure, circulatory disorders, spasms, ulcers and allergic reactions.

Furthermore, German Pat. No. 1,154,810 discloses verapamil (1,7-bis-(3,4-dimethoxyphenyl)-3-methylaza-7-cyano-8-methylnonane), whose action against arteriosclerosis has been investigated (JACC 1, (1983) 1453 and Am. J. Cardiol. 54 (1984), 884).

We have found that anipamil has a very good action against arteriosclerosis.

The present invention relates to the use of anipamil and its salts with physiologically tolerated acids for the preparation of drugs having antiarteriosclerotic properties and for use in the treatment of arteriosclerosis.

Anipamil can be used in the free form. Advantageously, however, it is employed in the form of a salt with a physiologically tolerated acid (cf. European Laid-Open Application No. 65,158).

Arteriosclerosis is a frequent disorder of the artery wall, which is caused by many factors and results in the formation of atheromas and hence in the constriction of the vascular system and vascular occlusion. The most important factors responsible for formation of atheromas are:

an increase in the permeability of the endothelium of the artery wall to macromolecules (lipoproteins)

migration of smooth muscle cells from the vascular muscle layer into the intima with subsequent proliferation and synthesis of ground substances (formation of arteriosclerotic plaque)

migration of macrophages which take up the lipoproteins penetrating in excessive amounts (foam cell formation).

The further course may involve disintegration of plaque tissue and deposition of calcium with mineralization, especially of the elastic fibers, and ruptures of the endothelium with hemorrhaging into the plaques and subsequent thrombosis of the affected vascular section (myocardial infarct, stroke).

With the compound according to the invention, the formation of atheromas in the vascular wall and the progress of arteriosclerotic changes can be inhibited or their regression promoted.

To demonstate the antiarteriosclerotic action, anipamil was administered orally and daily to male rabbits for 10 weeks. To induce arteriosclerosis, the animals received a diet which contained 2% of cholesterol. At the end of the test period, the animals were sacrificed. The aorta was removed between the aortic valve and the bifurcation of the iliac vessel, opened along the median line and stained with Sudan IV. The areas of the intima which had undergone arteriosclerotic changes and were stained red were determined planimetrically. The extent of the antiarteriosclerotic effect was determined by comparison with untreated control animals. The comparison substance used was verapamil.

In this test, anipamil inhibited the development of arteriosclerotic plaques after administration of only a quarter of the amount of substance required to achieve the same effect with verapamil.

Anipamil and its salts can be administered orally or parenterally in a conventional manner. The dose depends on the age, condition and weight of the patient and on the route of administration. As a rule, the daily dose of active compound is from about 0.1 to 1.0 mg/kg of body weight in the case of oral administration and from 0.01 to 1.0 mg/kg of body weight in the case of parenteral administration. Normally, daily doses of from 1 to 5 mg/kg are administered orally or rectally and from 0.05 to 0.25 mg/kg parenterally.

Anipamil and its salts can be employed in the conventional solid or liquid pharmaceutical forms, for example in the form of tablets, film tablets, capsules, powders, granules, coated tablets, suppositories, solutions or controlled dosage aerosols. These are produced in a conventional manner, and to do so the active compounds can be processed with the conventional pharmaceutical auxiliaries, such as tablet binders, fillers, preservatives, tablet disintegrants, flow regulators, plasticizers, wetting agents, dispersants, emulsifiers, solvents, retarding agents and/or antioxidants (cf. H. Sucker et al: Pharmazeutische Technologie, Thieme-Verlag, Stuttgart, 1978). The formulations thus obtained normally contain the active compound in an amount of from 0.1 to 99% by weight.

EXAMPLE 1

Tablets having the following composition are prepared by pressing on a tablet press in a conventional manner:
40 mg of anipamil hydrochloride
120 mg of corn starch
13.5 mg of gelatine
45 mg of lactose
2.25 mg of Aerosil ® (chemically pure silica in the form of submicroscopic particles)
6.75 mg of potato starch (as a 6% strength paste)

EXAMPLE 2

Coated tablets having the following composition are prepared in a conventional manner:
20 mg of anipamil hydrochloride
60 mg of core material
60 mg of sugar-coating material The core material consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consists of 5 parts of sucrose, 2 parts of corn starch, 2 parts of calcium carbonate and 1 part of talc. The coated tablets thus prepared are then provided with a coating resistant to gastric juice.

EXAMPLE 3

10 g of anipamil hydrochloride are dissolved in 5,000 ml of water with the addition of NaCl, and the solution is brought to pH 6.0 with 0.1 NaOH so that a blood-isotonic solution results. 5 ml portions of this solution are introduced into ampules and sterilized.

We claim:

1. A method for the treatment of arteriosclerosis in a patient comprising, administering anipamil or a physiologically acceptable salt thereof to a patient in need of said treatment in an amount sufficient to inhibit or promote regression of artereosclerotic changes or atheroma formation in the vascular wall.

* * * * *